United States Patent
Granger, Jr., deceased et al.

(10) Patent No.: US 6,175,234 B1
(45) Date of Patent: Jan. 16, 2001

(54) SELF-ALIGNING EDDY CURRENT PROBE HOLDER

(75) Inventors: Carl Granger, Jr., deceased, late of West Chester, by Janice L. Granger, executrix; David E. Day, Milford, both of OH (US); Thomas B. Hewton, Cape Coral, FL (US)

(73) Assignee: General Electric Company, Cincinnati, OH (US)

( * ) Notice: Under 35 U.S.C. 154(b), the term of this patent shall be extended for 0 days.

(21) Appl. No.: 09/154,882

(22) Filed: Sep. 17, 1998

(51) Int. Cl.[7] .......................... G01N 27/90; G01N 27/82; G01R 33/00
(52) U.S. Cl. .......................... 324/219; 324/226; 324/262; 73/866.5
(58) Field of Search ................ 324/219–221, 324/226, 234, 236–238, 262, 149, 758; 73/866.5, 661; 33/501.04, 501.5, 501.12, 542, 556, 558.01; 74/471 XY

(56) References Cited

U.S. PATENT DOCUMENTS

| | | |
|---|---|---|
| 3,234,455 | 2/1966 | Idel . |
| 3,600,678 * | 8/1971 | Garrett et al. ................... 324/72.5 X |
| 3,718,855 * | 2/1973 | Rogel et al. ..................... 324/234 X |
| 4,134,067 * | 1/1979 | Woodbury ............................ 324/219 |
| 4,827,771 | 5/1989 | Cary et al. . |
| 4,991,439 * | 2/1991 | Betts .................................. 73/661 X |
| 5,023,549 | 6/1991 | Dau et al. . |
| 5,136,240 | 8/1992 | Geier et al. . |
| 5,174,165 * | 12/1992 | Pirl .................................. 324/220 X |
| 5,279,168 | 1/1994 | Timm . |
| 5,424,639 * | 6/1995 | Meiffren et al. ..................... 324/219 |
| 5,442,286 | 8/1995 | Sutton, Jr. et al. . |
| 5,600,240 | 2/1997 | Mikhailovich et al. . |
| 5,834,937 * | 11/1998 | Burris .................................. 324/219 |
| 5,955,684 * | 9/1999 | Gravel et al. ....................... 73/866.5 |

* cited by examiner

Primary Examiner—Gerard Strecker
(74) Attorney, Agent, or Firm—Andrew C. Hess; Gerry S. Gressel

(57) ABSTRACT

An intermediary device is provided between an eddy current bolt hole inspection machine and an associated eddy current probe to positionally align the probe in each bolt hole to be inspected. A first end of the device is attachable to the eddy current bolt hole inspection machine, and a second end, having a tightening bolt, is attachable to the eddy current probe. A collet associated with the second end of the device secures the probe to the device when the tightening bolt is tightened subsequent to the second end accepting the eddy current probe. An adjustable flange component has a first portion separated from a second portion via a spring wave washer to allow the second portion to move left to right and front to back, relative to the first portion.

4 Claims, 2 Drawing Sheets

SELF-ALIGNING EDDY CURRENT PROBE HOLDER

TECHNICAL FIELD

The present invention relates to the inspection of hollow cylindrical structures, such as bolt holes, and, more particularly, to a device for holding and aligning a probe for inspecting such structures.

BACKGROUND OF THE INVENTION

Eddy current inspection probes are used for crack detection in bolt holes and the like. With the advent of high speed turbomachinery, a number of critical rotating parts are being specifically tested for cracks and related defects in their bolt hole walls. Various testing equipment have been developed to inspect for metal cracks in critical locations. Eddy current inspection is a commonly used technique for detecting discontinuities or flaws in the surface of components of a gas turbine engine.

The current method to inspect a bolt hole initially requires aligning a bolt hole inspection machine to the first bolt hole to be inspected. The existing bolt hole inspection machine is started and the system inspects a first bolt hole and automatically indexes to and inspects each subsequent bolt hole. However, in the course of manufacturing various components, bolt holes can vary slightly in spacing from a previous hole, by approximately 0.015" in any direction. It is critical with bolt hole inspection that the probe be held in a vertical position. If the alignment is at all inaccurate, the lift-off of the probe from inside of the bolt hole will give a (false) signal that the bolt hole will fail. The hole will have to be realigned and rerun to see if it will pass the limits that are set up for that part type. Every hole that fails on a part requires an additional three or more minutes to realign the probe to the hole and restart the inspection process. On average, an additional one to two hours is spent realigning the probe and restarting the inspection device due to false signals.

It would be desirable to be able to provide accurate alignment of the bolt hole inspection probe, compensating for variations in the spacing between holes. The objects, features and advantages of the present invention will become more readily apparent in the following description when taken in conjunction with the appended drawings.

SUMMARY OF THE INVENTION

The present invention provides a self-aligning probe holder whereby the probe is allowed to float in all directions to compensate for variations in spacing between holes. This allows the probe to stay vertical at all times, with very little lift off occurring.

In accordance with the present invention, an intermediary device is provided between an eddy current bolt hole inspection machine and an associated eddy current probe to properly align the probe in each bolt hole to be inspected. A first end of the device is attachable to the eddy current bolt hole inspection machine, and a second end, having a tightening bolt, is attachable to the eddy current probe. A collet associated with the second end of the device secures the probe to the device when the tightening bolt is tightened subsequent to the second end accepting the eddy current probe. An adjustable flange means has a first portion separated from a second portion via a spring wave washer to allow the second portion to move left to right and front to back, relative to the first portion.

In the drawings as hereinafter described, a preferred embodiment is depicted; however, various other modifications and alternative constructions can be made thereto without departing from the true spirit and scope of the invention.

BRIEF DESCRIPTION OF THE DRAWINGS

The novel features of the invention are set forth with particularity in the appended claims. The invention itself, however, both as to organization and method of operation, together with objects and advantages thereof, may best be understood by reference to the following description taken in conjunction with the accompanying drawings in which:

DETAILED DESCRIPTION OF THE INVENTION

Figure 1:
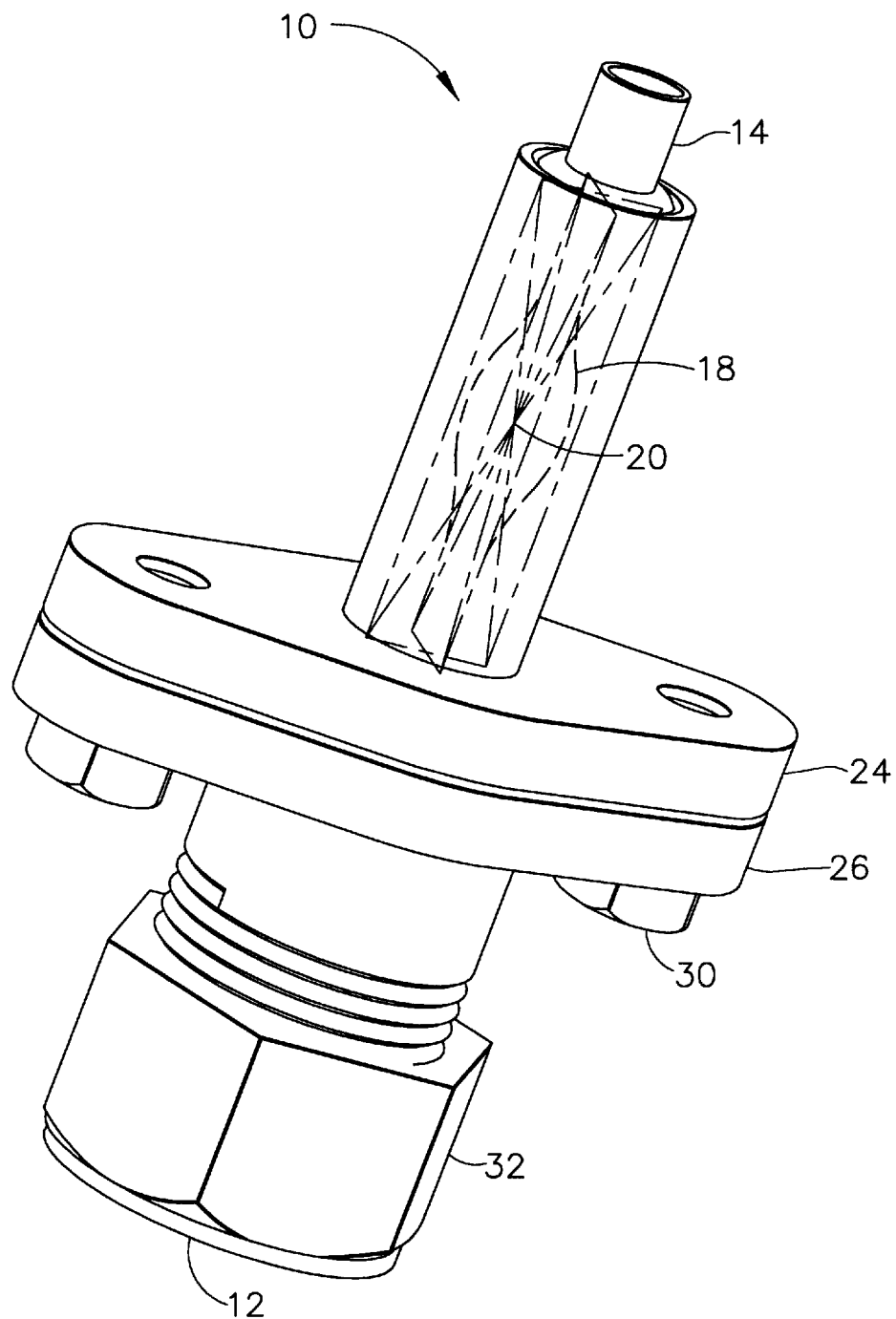
FIG. 1 is an isometric view of a self-aligning probe holder in accordance with the present invention.
Figure 2:
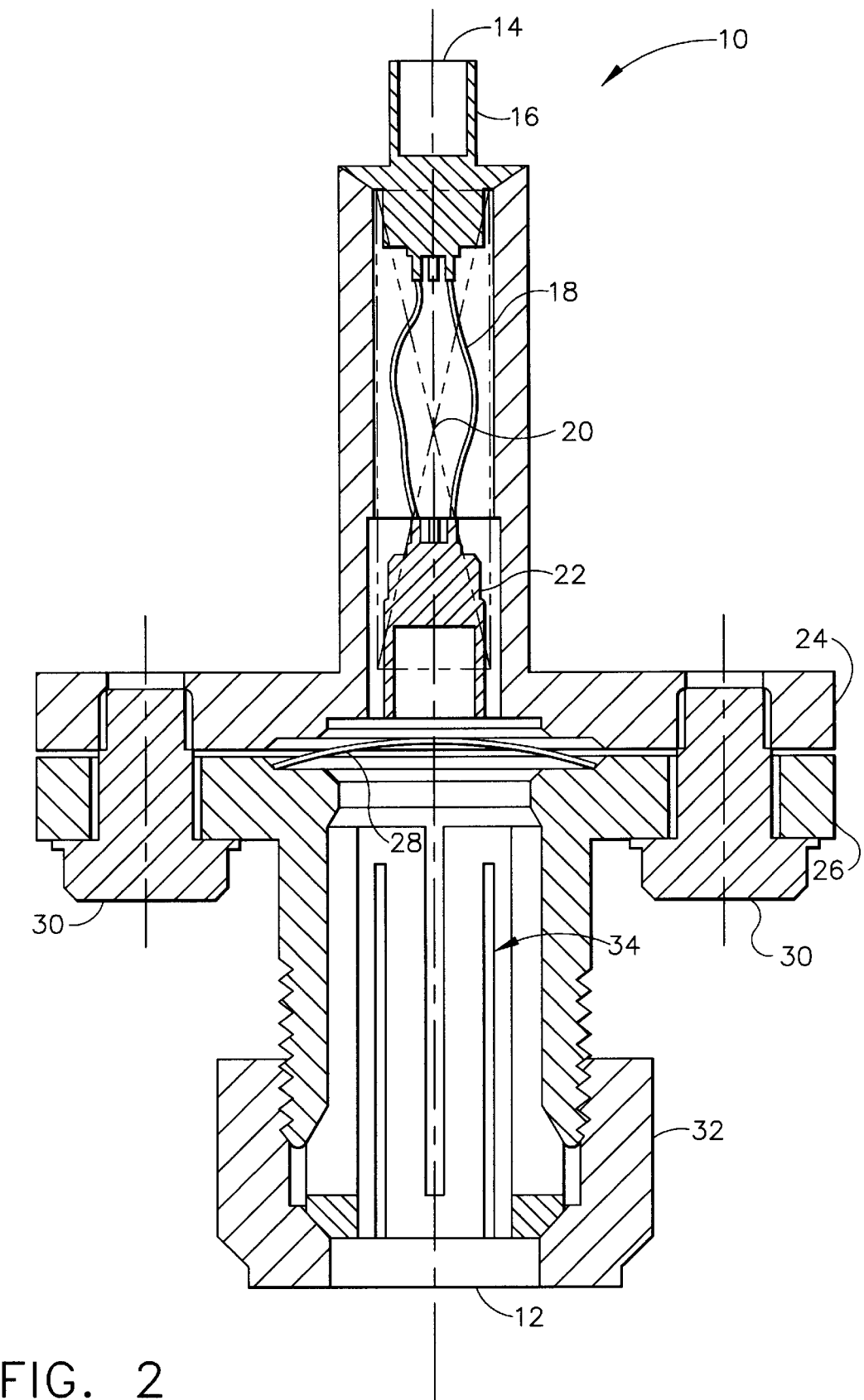
FIG. 2 is a cross-sectional view of the probe holder of FIG. 1.

The present invention will be described with respect to inspecting a bolt hole of a gas turbine engine component; those skilled in the art, however, will recognize that the principles of the present invention could be easily adapted or modified to inspect various other components, including any hollow cylindrical structure, requiring inspection.

Referring to the drawings, the probe holder 10 allows a probe, attachable at first end connection 12, to float in all directions, thereby compensating for variations in spacings of bolt holes of a gas turbine engine or the like. The opposite end 14 of the probe holder 10, is attachable to the eddy current probe machine, with male plug 16, wire 18, compression spring 20, and female plug 22 cooperating to achieve the necessary connection.

Initially, then, end 14 of the probe holder 10 is plugged into an existing bolt hole inspection machine, known to those skilled in the eddy current inspection art. The electrical connection at 14 is designed to be plug-compatible for any standard bolt hole probe machine that is currently being used in the industry to inspect bolt holes. An adjustable flange comprising area 24 and area 26, allows for the multi-directional floating capability of the probe holder 10. The area 24 and the area 26 are separated by a spring wave washer 28 that keeps the two pieces from contacting each other. This allows area 26 of the self aligning probe holder 10 to move left to right and front to back, relative to area 24. Bolts 30 only have enough clamping pressure to assure a snug fit, without applying so much pressure that areas 24 and 26 cannot be free from each other. In a preferred embodiment of the present invention, the total float will be a maximum of approximately 0.040".

With the self aligning probe holder 10 being held in the bolt hole inspection machine via connection 14, any conventional bolt hole probe can be installed at end 12. Nut 32 is tightened, thereby tightening collet 34. Collet 34 applies sufficient pressure to securely hold the probe in the probe holder device.

Areas 24 and 26 of the self-aligning probe holder 10 are two separate components that will float when a bolt hole probe is plugged into end 12. This float allows for bolt hole positional variations, eliminating the previously necessary time used to stop and realign the bolt hole probe during inspection.

Those skilled in the art will recognize that the present invention provides a novel device for holding and aligning a probe associated with a bolt hole inspection machine, for inspecting hollow cylindrical surfaces of a gas turbine engine component or the like. The self-aligning probe holder of the present invention allows the probe to float in all directions, preventing the problem of lift-off which occurs due to variations in bolt hole spacings and keeping the probe constantly vertical.

While preferred embodiments of the present invention have been shown and described herein, it will be obvious to those skilled in the art that such embodiments are provided by way of example only. Numerous variations, changes, and substitutions will now occur to those skilled in the art without departing from the invention and those skilled in the art will recognize that the principles of the present invention could be easily adapted or modified to inspect other components. Accordingly, it is intended that the invention be limited only by the spirit and scope of the appended claims.

What is claimed is:

1. An intermediary device is provided between an eddy current bolt hole inspection machine attached to a first end of the intermediary device and an associated eddy current probe receivable into a second end of the intermediary device opposite the first end, the device comprising:

a collet associated with the second end for securing the eddy current probe to the device after the eddy current probe is received into the second end; and an adjustable flange means comprised of a first component coupled to the first end and a second component coupled to the second end, the first and second components separated by a spring wave washer for allowing the second component and the eddy current probe to move left to right and front to back relative to the first component after securement of the eddy current probe to the device.

2. An intermediary device as claimed in claim 1 wherein the second end comprises a bolt wherein clamping pressure of the bolt allows the first and second component to maintain separation.

3. An intermediary device as claimed in claim 2 wherein the collet secures the eddy current probe to the device when a nut associated with the collet is tightened.

4. An intermediary device as claimed in claim 1 wherein the eddy current probe maintains a vertical position.

* * * * *